United States Patent [19]
Rybak

[11] 3,935,742
[45] Feb. 3, 1976

[54] LOW-INERTIA HYGROMETER

[76] Inventor: Boris Rybak, Universite de Caen Faculte des Sciences - Zoophysiologie, Caen, France

[22] Filed: Oct. 9, 1974

[21] Appl. No.: 513,180

Related U.S. Application Data

[63] Continuation-in-part of Ser. No. 369,457, June 13, 1973, abandoned.

[52] U.S. Cl............ 73/336.5; 128/2.08; 324/65 P; 338/35
[51] Int. Cl.².................................... G01N 27/04
[58] Field of Search............ 73/73, 336.5; 324/65 P; 338/34, 35; 340/235; 128/2.08, DIG. 29

[56] References Cited
UNITED STATES PATENTS

| | | | |
|---|---|---|---|
| 2,047,638 | 7/1936 | Kotz | 324/65 P |
| 2,563,341 | 8/1951 | Kettering | 200/61.06 X |
| 2,613,302 | 10/1952 | Gvrewitsch | 324/65 P |
| 2,813,242 | 11/1957 | Crump | 322/2 |
| 2,862,090 | 11/1958 | Mayer | 338/35 |
| 2,881,056 | 4/1959 | Joyner | 73/73 X |
| 3,045,198 | 7/1962 | Dolan et al. | 324/65 P |
| 3,204,418 | 9/1965 | Mathews | 73/336.5 |
| 3,232,288 | 2/1966 | Krobath | 128/DIG. 29 |
| 3,241,549 | 3/1966 | Tyler | 128/DIG. 29 |
| 3,299,387 | 1/1967 | Sanford | 324/65 P |
| 3,350,941 | 11/1967 | Misevich et al. | 348/235 X |
| 3,376,501 | 4/1968 | Peranio | 324/65 P |
| 3,540,278 | 11/1970 | Diamond et al. | 73/336.5 |
| 3,748,625 | 7/1973 | Bennewitz | 338/34 |
| 3,749,885 | 7/1973 | Nagasima | 340/235 |
| 3,868,492 | 2/1975 | Taylor | 73/336.5 |

FOREIGN PATENTS OR APPLICATIONS

| | | | |
|---|---|---|---|
| 1,466,834 | 3/1969 | Germany | 128/2.08 |

*Primary Examiner*—S. Clement Swisher

[57] ABSTRACT

The invention relates to a low-inertia hygrometer for controlling and measuring the hygrometric degree of a gaseous flux. The hygrometer includes two electrodes placed at a certain distance from one another and separated by a medium which, initially, is a poor conductor of electricity, but becomes electrically conductive when water vapour is present.

20 Claims, 3 Drawing Figures

LOW-INERTIA HYGROMETER

This application is a continuation-in-part application of my copending application Ser. No. 369 457, filed on June 13, 1973 now abandoned.

The present invention relates generally to a low-inertia hygrometer and has more specifically for its object a device and its associated arrangements permitting, in particular, the control of a gaseous flux, especially a ventilatory gaseous flux.

The invention is based on the principle that when a medium which is a dielectric one, is humidified, the said medium becomes electrically conductive at its surface or within its volume.

Actually, the device of the present invention uses two conductors fulfilling the function of electrodes, placed at a certain distance from one another and separated by a medium which is not a conductor of electricity, or is a poor conductor thereof, the said medium becoming electrically conductive during a variable period of time as a result of the presence of steam or even water.

The modification of the conductivity takes place proportionally to the moisture content up to the point of water saturation of the inter-electrode space. Thus, considering a medium with a definite temperature and a definite rate of humidity, any variation of the humidity of the incident flux produces a variation of the conductive state of the inter-electrode region. Besides, this inter-electrode region. Besides, this inter-electrode region may, according to the invention, be constituted by a great variety of elements.

The said region may simply be a gas such as air, in which case the device according to the invention operates in connection with an ohmmeter having a good sensitivity (e.g. in the $10^7$-ohm range). Under such conditions, the humid fluid flux governs the response connected with the relative humidification and desiccation.

According to another feature of the invention, the said inter-electrodes region may also be constituted by a rigid, semi-rigid, flexible, supply or viscous (deformable or undeformable) dielectric body, so that, in this case, it is the conductivity of the surface of the said body that varies, the water evaporation flux consecutive to the condensation flux of the said water determining the duration of constitution of the more or less transitory conductive layer mentioned above. In this case, the device of the invention includes advantageously a thread, strip or reed having, as far as possible, at least one smooth surface so as to reduce, in particular, the time evaporation, thus enabling a short response time to be obtained. In other words, the device according to the invention exhibits practically no inertia, and its response time is not greater than about 50 milliseconds. The electrodes are placed at a distance suitable for the conditions of use of the hygrometer, whatever the shape of the said surface or surfaces may be, either at the external surface of the dielectric body, or on an internal surface of such a body, or, in the case of a differential arrangement constituted, for instance, by a hollow tube, at both the external and internal surfaces (the device then operating with two, three or four electrodes depending upon the connections), or lastly, in the case of a multi-differential arrangement constituted, by way of non-limitative example, by a system of co-axial hollow tubes, at the various sensitive surfaces, in which case use is made of as many electrodes as is necessary.

In case the said dielectric body is constituted by a condensation-evaporation element such as a thread of, for instance, natural or artificial rubber or any plastics material having a cylindrical or parallelepiped-shaped cross-sectional area of, for instance, one square millimeter, the electrodes are advantageously secured at a distance on the order of one centimeter and either permanently or temporarily (small electrically-conductive metal clips being advantageously used in the latter case), so that any water vapour flux at any temperature (compatible with the maintenance of the basic properties of the dielectric body or member) produces, by way of water condensation and subsequent evaporation, a variation of the superficial electrical conductivity, thus governing the response of the device in time and amplitude. For example, the electrical resistance of a rubber thread is reversibly reduced, within about 50 milliseconds, from 450.000 MΩ at 25° C and about 50% humidity to 50 MΩ for a human ventilatory expiration flux; another example worthwhile mentioning is that of a reticule made from a thin resilient thread, the cross-sectional area of which is on the order of 0.1 mm$^2$, and the resistance of which is reduced from 600.000 to 400 MΩ under the same humidity conditions as in the foregoing example.

Where the dielectric body is constituted, for instance, by a ceramic or any other material capable of withstanding a relatively high adjustable temperature, the evaporation of the condensation water layer can be accelerated by inserting into the body of the material considered any heating system such as, for example, a heating resistor, an infra-red lamp or the like.

The present invention also covers the various measuring arrangements associated with the hygrometric pick-ups, as well as the various electrical energy supplying sources allowing the operation of the device and humidity measurements.

The invention will be better understood from the following description which is illustrated by the appended diagrammatic drawings given solely by way of example and in which.

Figure 1:
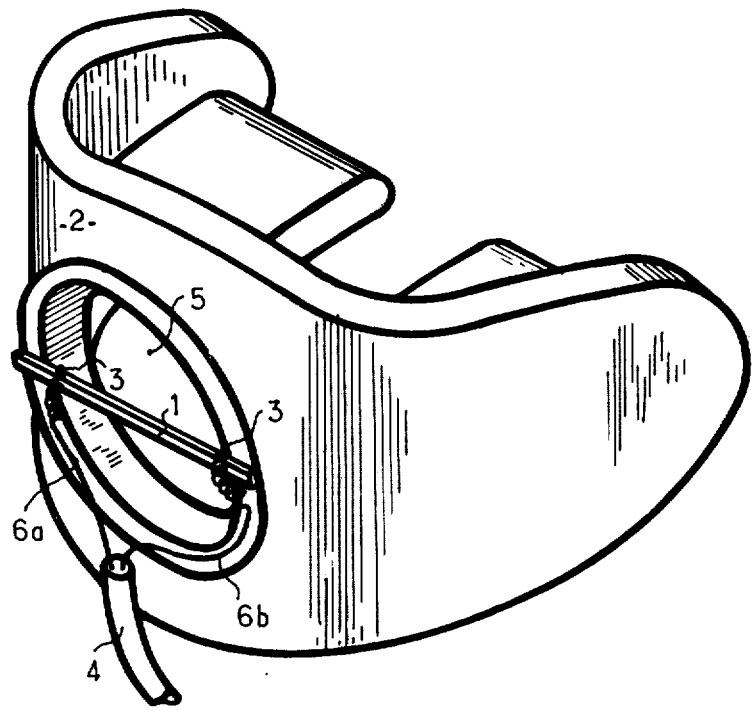
FIG. 1 is a perspective view of a mouthpiece, illustrating the application of the principle of the invention.

Referring to FIG. 1, there is illustrated an example of embodiment of the device of the invention used, in particular, for the control of the ventilatory rate and amplitude of human beings. The said device is constituted by an element 2 forming an oro-nasal mask or mouthpiece. The said element may be made from a rigid, semirigid, resilient or supple material of the type conventionally used for spirometry. The element 2 is not provided with an adduction tube, but simply with an opening 5 for mouth inspiration and expiration, the said opening having the advantage of offering no resistance to the ventilatory flux under ordinary control conditions. In the opening 5 is secured, by way of sticking, welding or the like, a dielectric member 1 which may be constituted by a rod, thread or like element which is smooth and has a square cross-sectional area of 1 square millimeter. As appears clearly from FIG. 1, the dielectric member 1 extends along a diameter of the opening 5, it being understood that the said opening may have any desired shape and that the said rod may be mounted in any desired manner on the said opening. The two end portions of the member 1 are provided with fixing points, welds or the like 3, for two conductors 6a, 6b placed in a common sheat 4. Alternatively, the conductor 6 may be connected to the member or rod 1 through small metal clips (not shown) since the device may be thrown away after the first use, owing to microbial sterility considerations and its very low cost.

Figure 2:
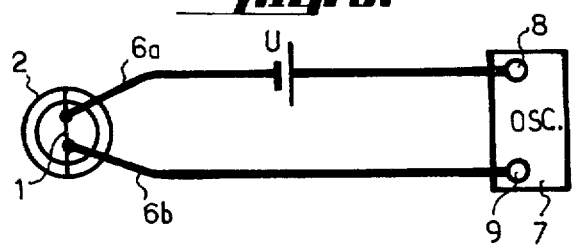
FIG. 2 is a diagrammatic view of one embodiment of the supply and measuring means associated with the device or mouthpiece of FIG. 1.

As already mentioned, various measuring arrangements and electrical power sources may be associated with the device of the invention. Some of such arrangements are shown in FIGS. 2 and 3 described hereafter:

In FIG. 2 is diagrammatically shown the dielectric member 1 provided with its two conductors 6a, 6b and mounted on the element 2. A battery U as electrical energy supplying means has a pole coupled to one of the conductors 6a, 6b, e.g. the conductor 6a. Indicating means 7, such as an oscilloscope for instance, are provided for displaying and/or recording an electrical signal and comprise two input terminals 8, 9, with the terminal 8 connected through the battery U to the conductor 6a and the terminal 9 directly connected to the conductor 6b.

The operation of the electrical circuit constituted by member 1, conductor 6a, battery U, oscilloscope 7, conductor 6b in series connection is as follows. When the surface of the smooth member 1 is not provoded with water condensation, substantially no current can pass through said member 1, thence through the oscilloscope 7. When some amount of water condensation is formed on the surface of the member 1 during exhalation, a current flows through said electrical circuit at a rate proportional to said amount of water condensation. However, due to the particular construction of the smooth dielectric member according to the invention, the water condensation can be evaporated in a very short time within about 50 ms., so that the current goes down to substantially zero in the same time. Accordingly, the current signal displayed by the oscilloscope 7 can be a substantially instantaneous image of the amount of water condensation on the member 1. In other words, the device according to the invention has a very low inertia. It will be appreciated that the sensitivity of such an arrangement is dependent upon the potential between the pole terminals of the battery U and is increased as this potential is raised. Experiments have been successful with e.g. an oscilloscope having an input resistance of about 1 M$\Omega$ and with a 9 volt battery.

Figure 3:
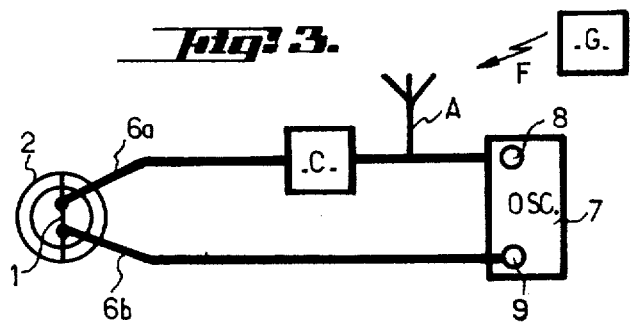
FIG. 3 is a diagrammatic view of a second embodiment showing in particular other supplying means which can be used with the device of FIG. 1.

FIG. 3 shows a preferred embodiment of the electrical circuit for measuring and displaying the breathing signal. More specifically, FIG. 3 illustrates an alternative embodiment of the electrical power supplying means in the measuring circuit, in substitution for the battery U in FIG. 2. In this arrangement, the power supply means comprises an antenna A which may be connected anywhere along one of the conductors 6a, 6b, e.g. conductor 6a, while the other conductor 6b could be grounded. The antenna A is adapted to receive an external electromagnetic field schematically indicated by arrow F. This external electromagnetic field may comprise the broadcast radio waves, and any spurious electrical signal or noise, such as the noise provided in an industrial area, or more specifically in a hospital center wherein the device of the invention can be advangeously used. Since the sensitivity of the arrangement is dependent upon the potential provided by the power supply means, it is required that the detected electromagnetic field be relatively stable. For this purpose, a clipper C for limiting the amplitude of the signal received from antenna A at a predetermined threshold may be advantageously provided as shown in FIG. 3. Another requirement for the electromagnetic field is due to the response time of the member 1 of the invention which, as disclosed hereabove, is within about 50 ms. Proper measurements involve of course an electromagnetic field having a frequency much greater that that corresponding to the response time.

Eventually where the antenna A provides a signal power lower than a predetermined level, an electromagnetic field generating device G may be disposed close to the antenna A for supplying it with a proper electromagnetic field. The device G may be for example a transmitter comprising for instance a multivibrator having a frequency determined in accordance with the response time. On the other hand, it is to be noted that the quality of measurements is dependent upon the sensitivity of the indicating means 7 which can advantageously be adjusted with the amplitude of the signal to be measured.

The device according to the invention has been disclosed hereabove as applying in particular to measurements of water vapour present during a breathing exhalation cycle. However such a device can be advantageously used for the evaluation of an electrically conductive fluid in many technical fields as explained hereinafter.

The apparatus according to the invention is of interest in biology in the broadest sense of the word and, by way of non-limitative example, in pedology, limnology, oceanography, microbiology, ecology (including behaviour ecology), fundamental and applied research in animal as well as plant physiology, pharmacodynamics and pharmacology, space research and under-sea research (e.g. diver's mask), ergometry, speleology, medical and veterinary clinics, for functional examinations, as well as pre-operatory, per-operatory and post-operatory ventilatory control, and also under ambulatory conditions. Moreover, the device according to the invention may be used in microphony, and also for the measurement of sudation either directly or by means of a gas-circulation sucker-chamber.

In addition, the device of the invention may be used as a "coughing appliance", in which case it is fitted to an oro-nasal mask under appropriate conditions.

Furthermore, the device of the invention may be used in all kinds of environment humidity controls such as, for instance:

a. in meteorology, b. in variable climate or unvariable climate premises, especially hot chambers, c. for the control of any water content such as the vapour water during any evaporation, more particularly ebullition, but also any steam or water vapour pressure (in the latter case, the device of the invention may be used as a water-level gauge), d. for the study of turbulent forced convections at the interactive atmosphere-ocean interfaces.

Generally, the device according to the invention is adaptable to any humidity control apparatus, either metabolic or non-metabolic. In this connection, it may serve as a humid contactor or cut-off switch in certain automatic electric regulations such as, for instance, water-bath thermo-regulation, by being placed at an appropriate predetermined distance for each heating temperature of the said bath.

Of course, the invention is by no means limited to the forms of embodiment described and illustrated which have been given by way of example only. In particular, it comprises all the means constituting technical equivalents to the means described as well as their combinations, should the latter be carried out according to the spirit of the invention.

What is claimed is:

1. Device for determining the rate and amplitude of breathing of an individual and comprising an element adapted for application to the face of an individual and being formed with an opening in the buccal or oronasal region of the face when said element is applied thereto, a unitary, integral elongate dielectric rod member of square cross-section and having end portions fixed to said element with its intermediate portion, between said end portions, disposed across said opening, said dielectric member having at least one smooth surface to accelerate evaporation of moisture from said member produced by the flux of water vapour present during a breathing exhalation cycle, said dielectric member being of a substance lacking electrical conductivity excepting when subjected to moisture during a breathing cycle during which its electrical conductivity varies in proportion to the amount of moisture exhaled during said cycle, a single pair of conductors connected to said dielectric member at said end portions thereof, electrical energy supplying means coupled to said single pair of conductors, and indicating means having two input terminals respectively coupled to said conductors for indicating the rate and amplitude of the electrical signal generated by said electrical energy supplying means through said dielectric member during the exhalation part of each breathing cycle.

2. A device according to claim 1, wherein said electrical energy supplying means comprises a battery inserted between one of said conductors and one of said input terminals of said indicating means.

3. A device according to claim 1, wherein said indicating means is an oscilloscope.

4. A device according to claim 1, wherein said electrical energy supplying means includes an external electromagnetic field and antenna means connected to one of said conductors for receiving said external electromagnetic field.

5. A device according to claim 4, comprising an electromagnetic field generating device for providing said external electromagnetic field, said device being disposed close to said antenna means.

6. A device according to claim 4, wherein said antenna means comprise amplitude clipping means for limiting the amplitude rate of the signals from said external electromagnetic field.

7. Device for determining the rate and amplitude of breathing of an individual and comprising an element adapted for application to the face of an individual and being formed with an opening in the buccal or oronasal region of the face when said element is applied thereto, a unitary, integral elongate dielectric thin resilient thread member having a cross-sectional area of 0.1 mm$^2$ and having end portions fixed to said element with its intermediate portion, between said end portions, disposed across said opening, said dielectric member having at least one smooth surface to accelerate evaporation of moisture from said member produced by the flux of water vapour present during a breathing exhalation cycle, said dielectric member being of a substance lacking electrical conductivity excepting when subjected to moisture during a breathing cycle during which its electrical conductivity varies in proportion to the amount of moisture exhaled during said cycle, a single pair of conductors connected to said dielectric member at said end portions thereof, electrical energy supplying means coupled to said single pair of conductors, and indicating means having two input terminals respectively coupled to said conductors for indicating the rate and amplitude of the electrical signal generated by said electrical energy supplying means through said dielectric member during the exhalation part of each breathing cycle.

8. A device for detecting a certain amount of an electrically conductive fluid comprising an unitary, integral elongate dielectric rod member of square cross-section and having end portions, and at least one smooth surface adapted to contact said conductive fluid, a single pair of conductors connected to said dielectric member at the end portions thereof electrical energy supplying means coupled to said single pair of conductors, and indicating means having two input terminals respectively coupled to said conductors for indicating the rate and amplitude of the electrical signal generated by said electrical energy supplying means through said dielectric member.

9. A device according to claim 8, wherein said electrical energy supplying means comprises a battery inserted between one of said conductors and one of said input terminals of said indicating means.

10. A device according to claim 8, wherein said indicating means is an oscilloscope.

11. A device according to claim 8, wherein said electrical energy supplying means includes an external electromagnetic field and antenna means connected to one of said conductors for receiving said external electromagnetic field.

12. A device according to claim 11, comprising an electromagnetic field generating device for providing said external electromagnetic field, said device being disposed close to said antenna means.

13. A device according to claim 11, wherein said antenna means comprise amplitude clipping means for limiting the amplitude rate of the signals from said external electromagnetic field.

14. A device for detecting a certain amount of an electrically conducted fluid comprising an unitary, integral elongate dielectric thin resilient thread member having a cross-sectional area of 0.1 mm$^2$ and having end portions, and at least one smooth surface adapted to contact said conductive fluid, a single pair of conductors connected to said dielectric member at the end portions thereof electrical energy supplying means coupled to said single pair of conductors, and indicating means having two input terminals respectively coupled to said conductors for indicating the rate and amplitude of the electrical signal generated by said electrical energy supplying means through said dielectric member.

15. A device according to claim 7, wherein said electrical energy supplying means comprises a battery inserted between one of said conductors and one of said input terminals of said indicating means.

16. A device according to claim 7, wherein said indicating means is an oscilloscope.

17. A device according to claim 7, wherein said electrical energy supplying means includes an external electromagnetic field and antenna means connected to one of said conductors for receiving said external electromagnetic field.

18. A device according to claim 14, wherein said electrical energy supplying means comprises a battery inserted between one of said conductors and one of said input terminals of said indicating means.

19. A device according to claim 14, wherein said indicating means is an oscilloscope.

20. A device according to claim 14, wherein said electrical energy supplying means includes an external electromagnetic field and antenna means connected to one of said conductors for receiving said external electromagnetic field.

* * * * *